United States Patent
Bond et al.

(10) Patent No.: US 8,309,929 B2
(45) Date of Patent: Nov. 13, 2012

(54) TUNABLE PHOTONIC CAVITIES FOR IN-SITU SPECTROSCOPIC TRACE GAS DETECTION

(75) Inventors: Tiziana Bond, Livermore, CA (US); Garrett Cole, Vienna (AT); Lynford Goddard, Champaign, IL (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 716 days.

(21) Appl. No.: 12/406,838

(22) Filed: Mar. 18, 2009

(65) Prior Publication Data

US 2009/0303487 A1    Dec. 10, 2009

Related U.S. Application Data

(60) Provisional application No. 61/037,642, filed on Mar. 18, 2008, provisional application No. 61/037,645, filed on Mar. 18, 2008.

(51) Int. Cl.
*G01J 5/02*    (2006.01)
(52) U.S. Cl. .................. 250/339.07; 356/432; 356/433; 356/437
(58) Field of Classification Search .................. 372/20; 256/437, 433, 432; 250/339.07; 385/12
See application file for complete search history.

(56) References Cited

U.S. PATENT DOCUMENTS

2004/0202400 A1* 10/2004 Kochergin et al. .............. 385/12
2011/0253909 A1* 10/2011 Himmelhaus et al. ..... 250/492.1

OTHER PUBLICATIONS

Bond et al., "Photonic MEMs for NIR in-situ Gas Detection and Identification," UCLR-Conf-232534, Sensors, 2007 IEEE published Jul. 6, 2007, Retrieved from internet [Aug. 30, 2011], from url <https://ieeexplore.ieee.org/xpls/abs_all.jsp?arnumber=4388666& tag=1>.*

Harris et al., "Micromachined tunable optoelectronic devices for spectroscope applications," Advanced Lasers and Their Applications, Holdberg and Lang., vol. 31 of OSA Trends in Optics and Photonics (Optical Society of America, 1999), Retrieved from internet [Aug. 29, 2011], from url <http://snow.stanford.edu/~wayne/pubs/tops.pdf>.*

Nohana Arsad et al., "Intra-Cavity Spectroscopy Using Amplified Spontaneous Emission in Fiber Lasers," Journal of Lightwave Technology, vol. 29, No. 5, published Mar. 1, 2011, p. 782; Retrieved from internet [Feb. 15, 2012]; Retrieved from url <http://ieeexplore.org/stamp/stamp.jsp?arnumber=05677567>.*

Evan Thrush et al.,"Integrated Semiconductor Vertical-Cavity Surface-Emitting Lasers and PIN Photodetectors for Biomedical Fluorescence Sensing," IEEE Journal of Quantum Electronics, vol. 40, No. 5, pub. May 5, 2004, p. 491; Retrieved from internet[Feb. 17, 2012]; Retrieved from url<http://www.breault.com/resources/kbasePDF/wp_ieee_001_integrated.pdf.*

* cited by examiner

*Primary Examiner* — David Porta
*Assistant Examiner* — Yara Green
(74) *Attorney, Agent, or Firm* — John P. Wooldridge

(57) ABSTRACT

Compact tunable optical cavities are provided for in-situ NIR spectroscopy. MEMS-tunable VCSEL platforms represents a solid foundation for a new class of compact, sensitive and fiber compatible sensors for fieldable, real-time, multiplexed gas detection systems. Detection limits for gases with NIR cross-sections such as $O_2$, $CH_4$, $CO_x$ and $NO_x$ have been predicted to approximately span from $10^{ths}$ to 10s of parts per million. Exemplary oxygen detection design and a process for 760 nm continuously tunable VCSELS is provided. This technology enables in-situ self-calibrating platforms with adaptive monitoring by exploiting Photonic FPGAs.

16 Claims, 7 Drawing Sheets

TUNABLE PHOTONIC CAVITIES FOR IN-SITU SPECTROSCOPIC TRACE GAS DETECTION

This application claims priority to U.S. Provisional No. 61/037,642, filed Mar. 18, 2008, titled: "Tunable Photonic Cavities for In-Situ Spectroscopic Trace Gas Detection," incorporated herein by reference. This application claims priority to U.S. Provisional No. 61/037,645, filed Mar. 18, 2008, titled: "Resonant Optical Transducers for In-Situ Gas Detection," incorporated herein by reference.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to methods for detecting gas, and more specifically, it relates to absorption spectroscopy as a mechanism for gas detection.

2. Description of Related Art

Gas analysis is conventionally performed using laboratory analytical techniques, e.g., gas chromatography or mass spectrometry (GC-MS), which do not satisfy current device and material constraints for unattended, flexible ground sensors, or for lightweight, highly sensitive systems for avionic operations. Absorption spectroscopy is a powerful alternative approach for gas in-field detection and identification, and several interesting techniques have been developed including tunable diode laser absorption spectroscopy (TDLAS). Typically, this occurs in the infrared (IR) region of the spectrum. Recently, micromechanically tunable vertical-cavity surface-emitting lasers (VCSELs) have been implemented in such fashion for near infrared (NIR) spectroscopy. Unfortunately, many existing TDLAS systems exhibit drawbacks that limit their deployment, including the need for cryogenic cooling, a requirement for a bulky multipass cell, or a long hollow or porous fiber with a relatively slow time response.

SUMMARY OF THE INVENTION

It is an object of the present invention to use extended cavity MEMO tunable optoelectronic devices for detection of gas.

This and other objects will be apparent based on the disclosure herein.

Embodiments of the present invention provide sensing techniques and apparatuses that combine photonics and widely-tunable microelectromechanical systems (MEMS) for sensing, detecting and monitoring of gas emissions for critical environmental, medical, and industrial applications. MEMS-tunable vertical-cavity surface-emitting lasers (VCSELs) can be exploited for in-situ detection and NIR spectroscopy of a variety of gases (e.g., $O_2$, $N_2O$, $CO_x$, $CH_4$, HF, HCl), with estimated sensitivities at the ppm level on footprints $\sim 10^{-3}$ $mm^3$. With MEMS-tunable VCSELs, wavelength tuning is realized through the actuation of a suspended Bragg reflector, resulting in physical variation of the optical path length and wavelength tuning ranges on the order of tens of nanometers. Given the short axial length of a typical VCSEL, displacement of the suspended mirror is capable of producing continuous tuning of a single lasing mode. The VCSELs can be electrostatically tuned with a continuous wavelength shift up allowing for unambiguous NIR signature determination. Selective concentration analysis in heterogeneous gas compositions is enabled, thus paving the way to an integrated optical platform for multiplexed gas identification by material and device engineering. An exemplary 760 nm AlGaAs based tunable VCSEL embodiment for $O_2$ detection is described.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Embodiments of the present invention use an extended cavity (EC) MEMS-tunable VCSEL in which the epitaxial materials structure is engineered to align the laser emission to a specific absorption wavelength (coarse tuning). Additionally, these devices incorporate a micromechanically tunable optical cavity that allows for scanning of the emission wavelength over a wide and continuous range, allowing access to multiple absorption lines of the gas (fine tuning). In addition, when gases without a significant NIR signature are to be detected, complimentary techniques can be implemented on the same platform. Functionalizing the cavities with gas-sensitive coatings allows for enhanced detection through a change in the optical response of the coating (e.g., index shift, change in absorption). Resonant cavities with high quality factor (Q), amplify the magnitude of these changes. Cavity ring down spectroscopy (CRDS) can be implemented to increase the sensitivity.

Devices have recently shown promise as a high-performance alternative to standard VCSELs for optical gas sensing, with demonstrations of the detection of carbon monoxide and carbon dioxide, as well as ammonia, at the telecom-relevant wavelength range near 1550 nm in external TDLAS. Following this path of research, the present inventors developed the first MEMS-tunable VCSELs with emission wavelengths below 800 nm. These devices operate within the oxygen A-band (760-780 nm), a relevant wavelength range for diode-laser-based oxygen detection.

Oxygen sensors are very important in controlling automotive and industrial emission processes for lower pollution and better yields, as well as improving flight safety. Concentration monitoring is also very important for biosensors in clinical diagnosis.

Figure 1A:
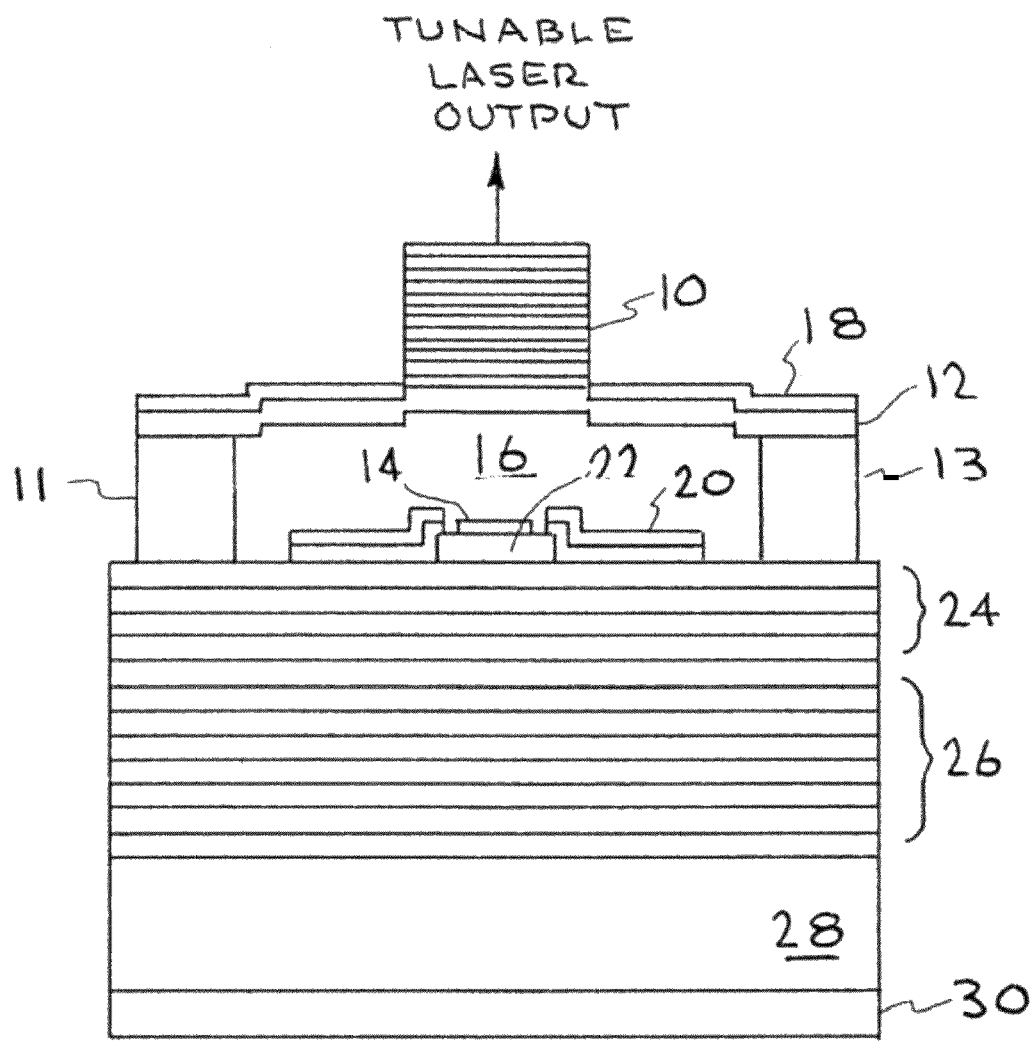
FIG. 1A shows a cross-sectional schematic of a MEMS tunable EC-VCSEL.
Figure 1B:
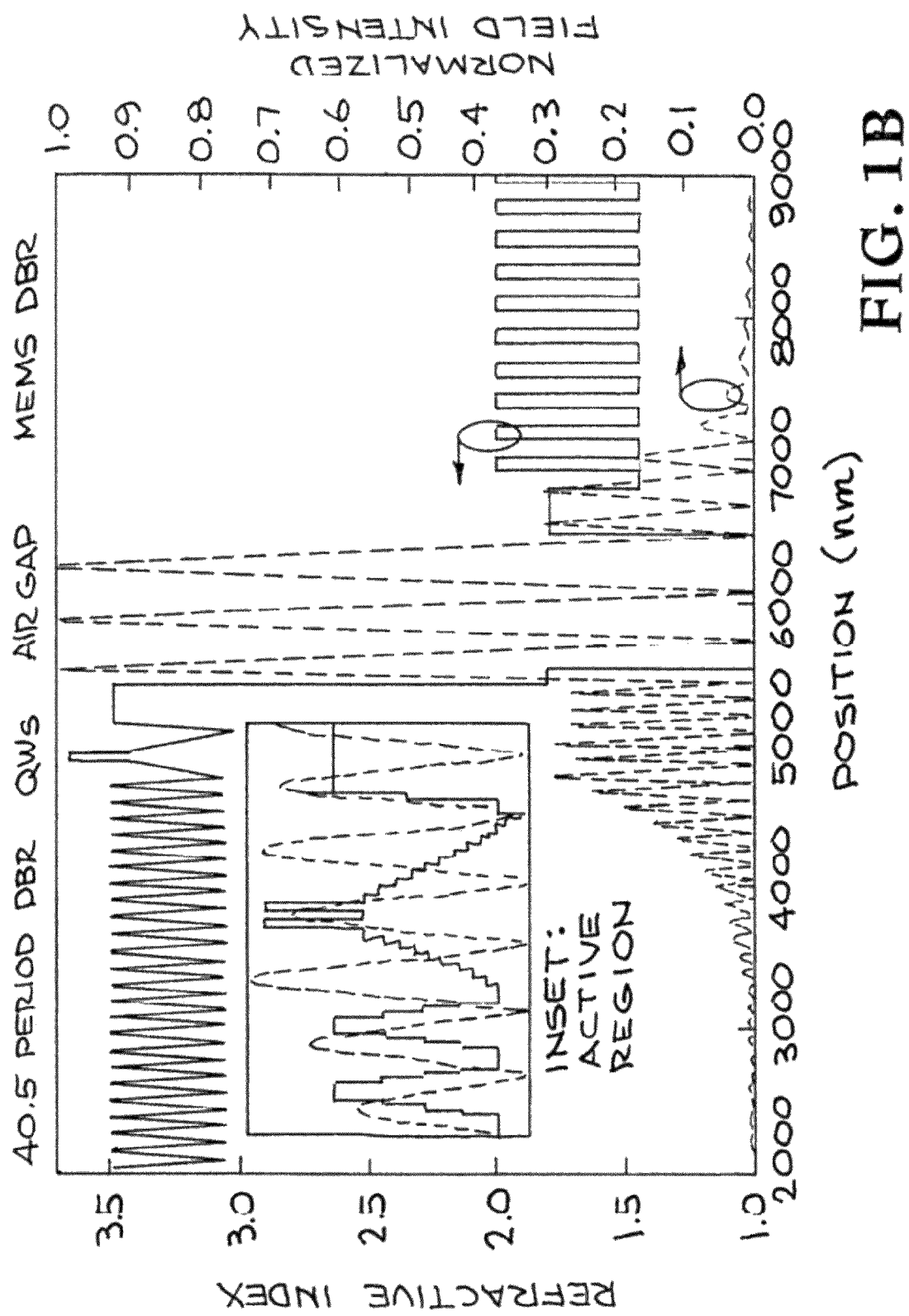
FIG. 1B shows the refractive index profile and electric field intensity generated with a transmission matrix model of an embodiment of the MEMS tunable EC-VCSEL of FIG. 1A.

The operation of the tunable-VCSEL-based gas sensor can be described as a multipass cell with optical gain. FIG. 1A shows a cross-sectional schematic of an exemplary MEMS tunable EC-VCSEL for $O_2$ sensing. The presence of gas in the air gap quenches the laser emission when the resonance wavelength is tuned to correspond with an appropriate absorption line. In operation, the laser is electrically driven above the lasing threshold and the gas flowing through the air gap spoils the gain-loss balance necessary for lasing by increasing the absorption losses within the cavity. In this case, the high-Q of the VCSEL structure enhances absorption as the light is reflected (>100 times) within the resonant cavity, between the top and bottom distributed Bragg reflectors (DBRs). During operation, the lasing power can be monitored remotely via transmission through an optical fiber or directly via an integrated detector. FIG. 1B shows the refractive index profile and electric field intensity generated with a transmission matrix model of an embodiment of the MEMS tunable EC-VCSEL of FIG. 1A. Note that the composition grading is continuous, but is represented as discrete steps in order to simplify the simulation.

Figure 2A:
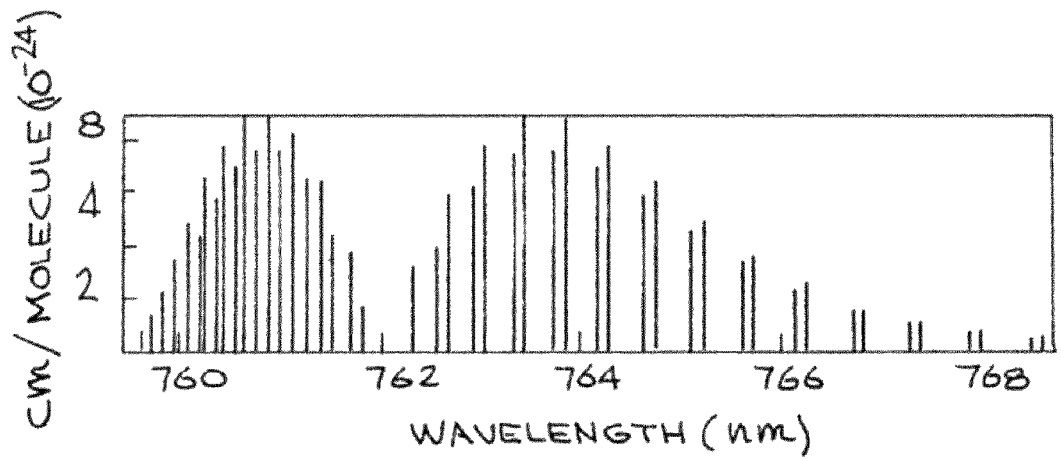
FIG. 2A shows the absorption signature of $O_2$ at 760 nm.
Figure 2B:
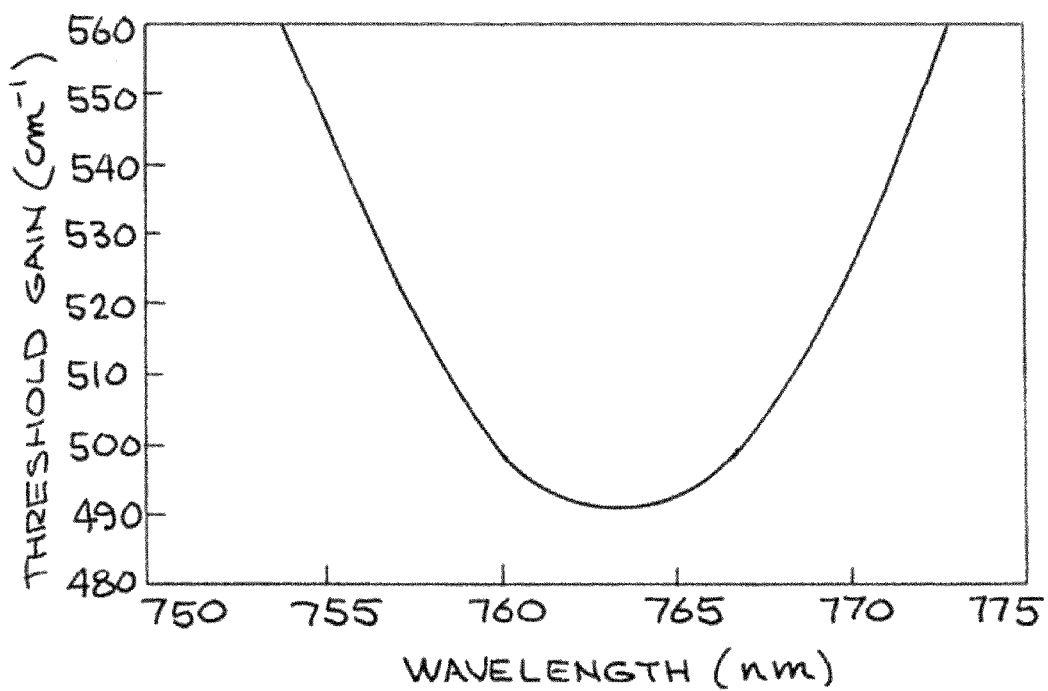
FIG. 2B shows continuous emission tuning of an exemplary laser according to the present invention.

In order to efficiently and selectively detect the signature absorption lines of the gas of interest, an appropriate tunable optical cavity is designed. The absorption cross-section of $O_2$ around 760 nm is shown in FIG. 2A. In one embodiment, the laser linewidth ($\delta\lambda$) of a tunable VCSEL is designed to be <1 pm within a full scanning range of at least 10 nm. The actuation voltage is designed to be <10 V and the power consumption is designed to be on the order of tens of mWs. As shown in FIG. 2B, the threshold gain vs. wavelength is calculated showing the capability of continuous tuning over 20 nm within the wavelength range of interest. Dynamic mode-hop free tuning is inherent in MEMS-tunable VCSELs due to the extremely short axial cavity length. Thus, the wavelength resolution of the tunable laser is limited by the voltage source driving the electrostatic actuator, the stability of the micromechanical system, and the resolution of the read-out system.

The presence of gases in the VCSEL air gap affects the amplification factor or round trip enhancement of the power flow in the laser structure and thus the variation of output power when compared with the quiescent state $P_0$:

$$\frac{\Delta P}{P} = \frac{P_0 - P}{P_0} \propto \frac{A_0 - A}{A_0}. \quad (1)$$

The amplification factor in absence of any gas is given by:

$$A_0 = (1 - \exp(-\delta_g L_{Cavity}))^{-1} \quad (2)$$

where $\delta_g = \alpha_0 - \Gamma g$ is the margin between the losses and the net modal gain of the laser. Similarly to the Beer-Lambert law, the absorption of the chemical specie is accounted in A through the relative gas cross-section $\sigma_{gas}$:

$$\alpha_{gas}(cm^{-1}) = \sigma_{gas} C \quad (3)$$

where C is the volume concentration of the gas specie. In such case $\delta_g$ becomes equal to $\alpha_0 + \alpha_{gas} - \Gamma g$.

The limit of detection (LOD) of the sensor platform is determined by a combination of the device and read-out system sensitivity. Considering a conservative instrumentation resolution limit of $\Delta P/P = 10^{-3}$, a first-order analytical analysis of laser sensitivity helped estimating that for $O_2$, with a cross-section sextion $\sigma_{NIR}$ ~10-21 $cm^2$/molecule (at room temperature and 1 atm pressure), at the operation wavelength of 760 nm, an LOD ~20 ppm of volume in air can be obtained with a air-gap thickness of 5 µm. If the analysis is extended to other gases with higher NIR cross-sections, such as $CO_x$, $CH_4$, $NO_x$, HF, HCl, the LOD is very promising showing sensitivities to a few ppm, as shown in TABLE I. For thicker air-gaps the sensitivity would increase.

TABLE I

Estimated limits of detection in the NIR

| Gas | λ (µm) | σ ($cm^2$/mol) | LOD |
|---|---|---|---|
| $O_2$ | 0.76 | $10^{-21}$ | 20 ppm |
| HF | 1.27 | $10^{-19}$ | 0.1 ppm |
| $N_2O$ | 1.38 | $10^{-21}$ | 10 ppm |
| CO | 1.57 | $10^{-21}$ | 50 ppm |
| $CH_4$ | 1.65 | $10^{-20}$ | 1 ppm |
| HCl | 1.75 | $10^{-19}$ | 0.1 ppm |

Figure 3A:
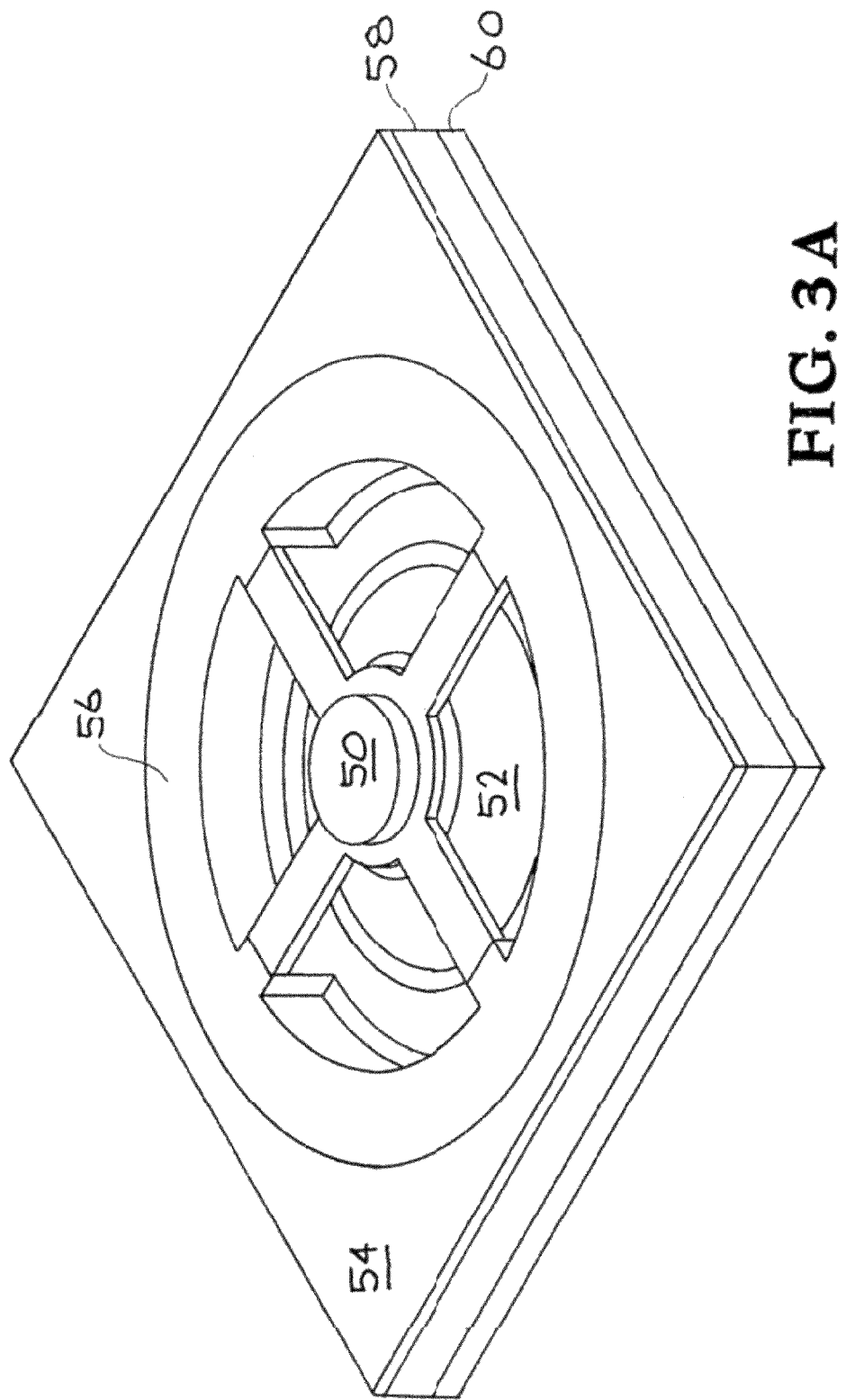
FIG. 3A shows a 3-D model of an embodiment of the tunable VCSEL.
Figure 3B:
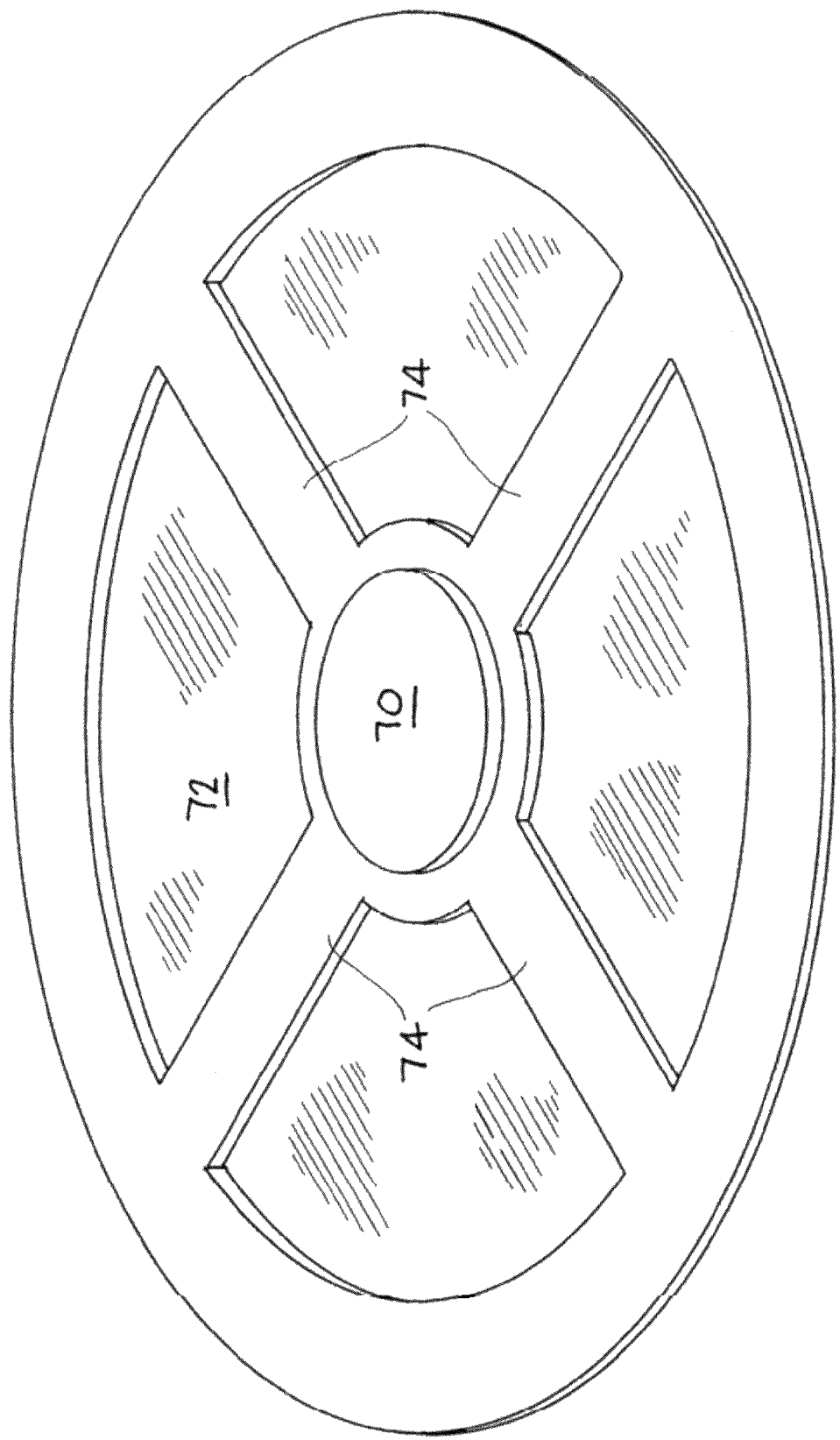
FIG. 3B shows a SEM picture of tunable membrane of the present invention.

FIG. 3A displays a solid model exemplary tunable-VCSEL-based $O_2$ sensor. Note that the scale of the air gap has been exaggerated to clarify the free-standing nature of the micromechanical structure. Some of the elements shown in the figure include a suspended $SiO_2/TiO_2$ DBR 50, VCSEL p-contact 52, MEMs top contact 54, undercut protection 56, VCSEL epi layer 58 and bottom contact 60. FIG. 3B shows a SEM picture of a tunable membrane and shows a suspended $TiO_2/SiO_2$ DBR, VCSEL p-contact/electrostatic actuator lower electrode and the membrane structure. As opposed to the all-epitaxial devices, embodiments of the tunable mirror design may incorporate an all dielectric structure, consisting of a silicon nitride ($SiN_x$) membrane and an evaporated dielectric DBR. The use of the dielectric suspended mirror allows for the development of a platform-independent tuning mechanism that is capable of being integrated with various vertical-cavity laser and detector active materials including the III-P, III-Sb, and III-N materials systems. The flexibility in operating wavelength afforded by the use of low-temperature deposited dielectrics is useful for gas sensing applications where key absorption lines may span a region larger than that attainable by a single materials system.

Figure 4A:
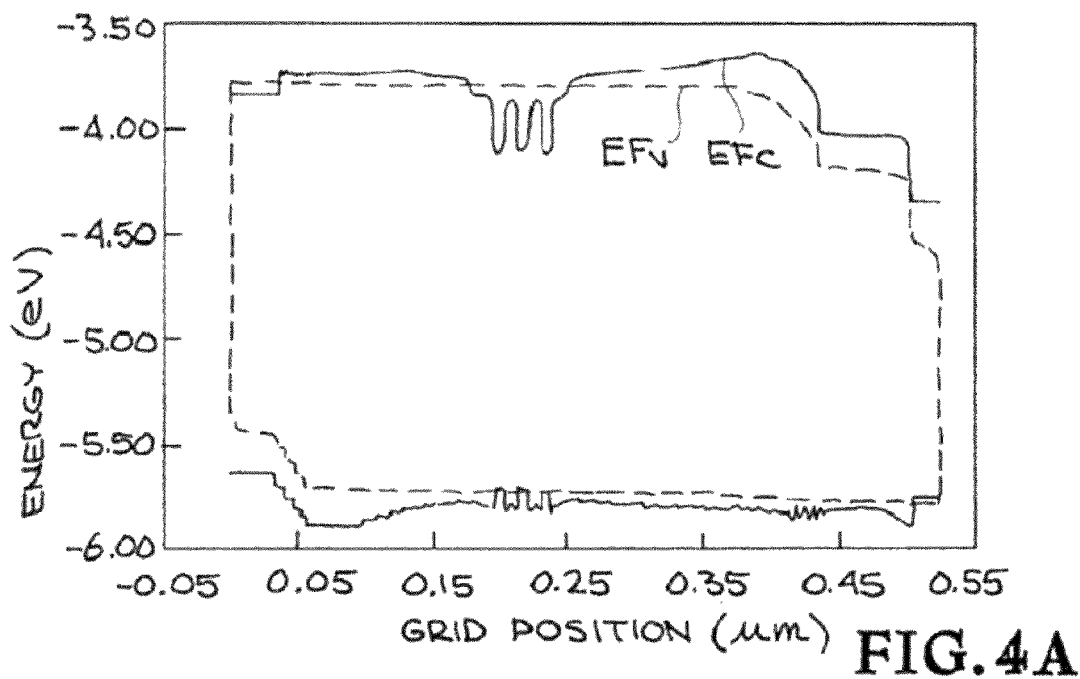
FIG. 4A shows a band diagram of an exemplary VCSEL active region at 2 V bias.

For the tunable VCSEL, the suspended mirror structure in one embodiment is built atop a 760 nm AlGaAs "half-VCSEL". Again, FIG. 1A shows a cross-sectional schematic of a tunable VCSEL usable in some embodiments of the present invention. The non-planarity in the suspended membrane arises from the transfer of the mesa geometry through the evaporated Ge film. FIG. 1B shows the refractive index profile as well as the electric field intensity, which is generated with a transmission matrix model. The AlGaAs epitaxial structure consists of a 40.5 period bottom DBR—with linear composition grading between the high index ($Al_{0.30}Ga_{0.70}As$) and low index ($Al_{0.92}Ga_{0.08}As$) layers—and an active region incorporating three 8 nm $Al_{0.14}Ga_{0.86}As$ quantum wells (QWs) separated by 10-nm thick $Al_{0.40}Ga_{0.60}As$ barriers (see the band diagram shown in FIG. 4A). The peak gain of the active region is designed to be near the absorption maxima of molecular $O_2$ in this wavelength range, as shown in FIG. 4A. Due to the strong absorption of the GaAs substrate, the VCSEL is constrained to be top emitting, in this case through the MEMS-tunable mirror structure. Ohmic contacts to the VCSEL are provided by a Ti/Pt/Au p-contact annulus and a blanket deposited Ge/Au/Ni/Au contact on the backside of the n-doped substrate. Carrier and optical confinement are realized by non-selectively wet etching a shallow mesa and oxidizing an exposed $Al_{0.98}Ga_{0.02}As$ layer.

From the top down, the suspended mirror structure consists of an evaporated dielectric DBR pillar 10 (from a minimum of 7 up to 13 periods of $TiO_2/SiO_2$) on top of a tensile stressed (328 MPa) $SiN_x$ structural film 12 deposited via plasma-enhanced chemical vapor deposition (PECVD). The combination nitride membrane is added as a high index quarter-wave layer. In order to realize the extended cavity structure, a single film anti-reflection coating 14 is included at the interface between the gain medium and gap 16 (e.g., an air gap) to eliminate coupled-cavity effects. Including the large index discontinuity between the nitride membrane and air gap, the peak reflectivity of the top DBR is calculated to be at least 0.997 for a stack with 7.5 periods or more.

For tuning of the emission wavelength, the device incorporates an integrated micromechanical actuator. An applied bias across the aluminum contact 18 on top of the $SiN_x$ structural film and the p-contact 20 on the VCSEL mesa 22 creates an electrostatic force that displaces the suspended mirror towards the substrate, reducing the optical path length and blue-shifting the resonance wavelength. The mirror is suspended on α-Ge pillars 11 and 13 atop the VCSEL mesa 22, atop quantum wells 24, atop DBR 26, atop n-doped GaAs substrate 28, atop the n-contact 30 of Ge/Au/Ni/Au. The materials of this VCSEL are exemplary. As mentioned previously, because of the short cavity length of the VCSEL, wide and continuous single-mode tuning is possible in these devices. Previous demonstrations of electrically injected tunable VCSELs utilizing the EC-design (emitting within the telecom relevant wavelength range near 1550 nm) have demonstrated tuning ranges approaching 70 nm. In embodiments of the present invention, the use of the integrated electrostatic actuator allows for a rapid tuning response. The tuning response for a 13.5 period MEMS-tunable VCSEL for a constant laser drive current of 2.4 mA includes lasing operation that occurs discontinuously over a range of 30 nm, from 767-737 nm. It is assumed that the cessation of lasing operation is due to additional loss within the cavity arising from non-uniform deflection of the suspended mirror.

Figure 4B:
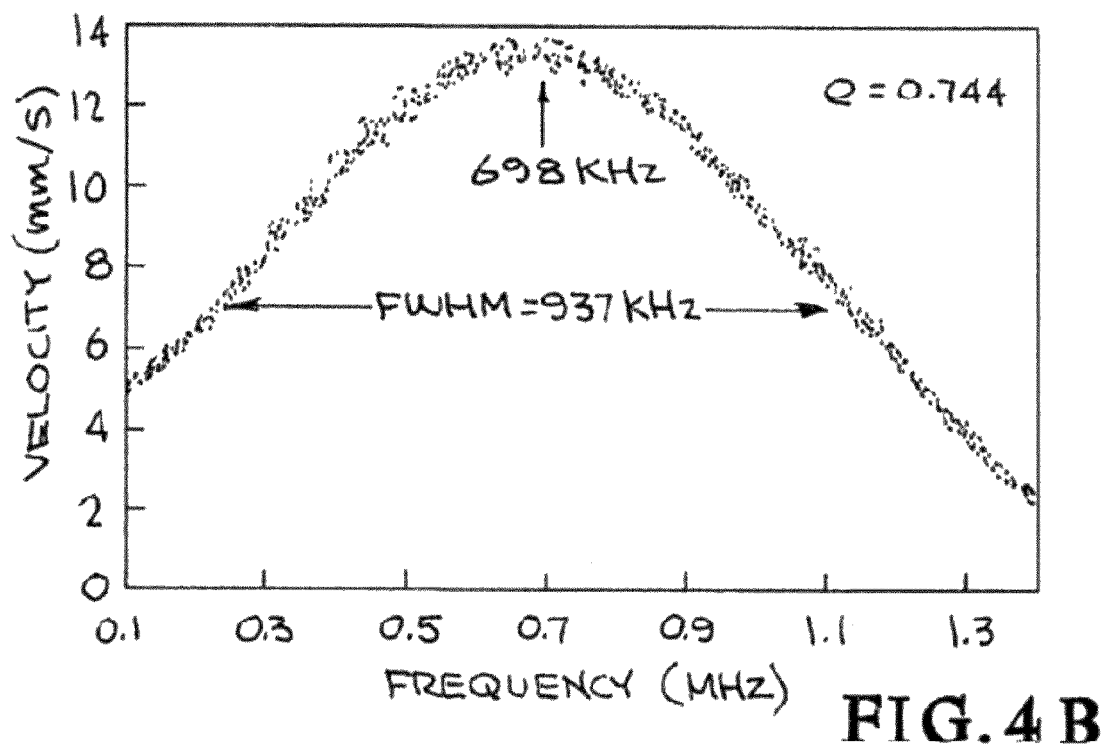
FIG. 4B shows a typical frequency response for a 13.5 period suspended mirror structure at atmospheric pressure

Characterization of this micromechanical structure has demonstrated a near critically-damped response at atmosphere with a wavelength tuning time of <10 µs. A MEMS motion characterization system consisting of a microscope-coupled laser Doppler vibrometer (LDV) is employed. FIG. 4B shows a typical frequency response for a 13.5 period suspended mirror structure at atmospheric pressure. Due to the large ratio of lateral dimensions to air-gap thickness, damping is dominated by squeeze film effects. The actuator examined here exhibits a mechanical resonance at 698 kHz with a Q of 0.74. For continuous scanning applications this device can sweep the desired tuning range at rates exceeding 1 MHz, while for step and hold applications, the settling time (defined as ±5% of final displacement) is 850 ns.

For gases lacking significant NIR signatures, such as $H_2$, the detection sensitivity can be enhanced by adding a gas specific coating to the optical cavity. Appropriate coatings include $WO_3$, $SnO_2$, PdO, ZnO, porous Si, for use in monitoring, e.g., $NO_x$, CO, $H_2S$ and $Cl_2$. These coatings will exhibit changes in refractive index when exposed to the appropriate target gas species, resulting in a measurable wavelength shift in the laser output spectrum.

Embodiments of the invention can be extended to several material systems in the visible, as well as the short wavelength infra-red (SWIR) range (2-3 µm) where molecules have higher absorption cross-sections. Recent developments have led to the demonstration of micromechanically-tunable filter structures integrated with HgCdTe materials structures for widely tunable resonant detectors in this wavelength range. Additionally, the technology has the potential of being extended to highly sensitive CDRS by integrating active (laser, detector) and passive devices (low loss filters) on the same platform.

As another example, consider a well-studied gas, $CO_2$, which signatures and observation in the NIR are well documented in literature. In order to be able to efficiently and selectively detect the spectral range and signature lines (Δλ separation and δλ linewidth) of the gas of interest, the DBR cavity is designed to have a Stop Band greater than the spectral range, with a resonance FWHM comparable or smaller than Δλ and less than Δλ tuning. As shown in FIG. 5A, these requirements are satisfied for $CO_2$ detection centered at 1570 nm with a resolution of δλ<1 pm, and a tuning Δλ<1 nm, within a full scanning range of 20-50 nm achieved with an actuation voltage of <20V and an applied laser power corresponding to only a few milliwatts.

The particular structure for the $CO_2$ can be constructed entirely in single-crystalline III-V heterostructures; previous devices have been realized in epitaxial films of GaAs and InP. In these materials systems, tunable VCSELs can be constructed on chip as small form factor 2-D arrays using standard semiconductor fabrication techniques (typical devices span approximately 250 µm). Because of the small mass of this structure ($<5\times10^{-11}$ kg) these membranes exhibit resonance frequencies of 0.25 MHz. In this case the entire wavelength span can be covered in <5 µs.

Some first qualitative analysis of the sensitivity of the lasers used by the inventors showed that for $CO_2$ with a cross-section $\sigma_{NIR}=10^{-21}$ cm²/molecule, at the operation wavelength of 1560 nm, a LOD <10 ppm of volume in air could be potentially obtained with a gap L=10 µm, which is significant, even with a very conservative assumption that the instrumentation resolution limit is ΔP/P $10^{-3}$ where P is the measured output power before and after quenching by the gas.

The sensitive detection occurs within a miniaturized volume. Indeed, the volume of the VCSEL herein considered for spectroscopy is only ~50×50×15 µm³, which is much less than the volume of a sugar cube or a cubic centimeter NO. By scaling the LOD by the involved path lengths, embodiments of the present invention enable many orders of magnitude of improvement within an enormously smaller footprint. It should be noted that by engineering the bandgaps of the III-V semiconductors even further, lower frequencies towards the SWIR (short wavelength IR) can be achieved for higher sensitivity.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:
1. A method for detecting a gas, comprising:
    electrically driving above a lasing threshold an extended cavity vertical cavity surface emitting laser to produce laser emission light at a wavelength and a power, wherein said laser includes a microelectromechanically tunable optical cavity;
    placing said laser in a position of interest; and
    tuning said optical cavity to produce a second wavelength that corresponds to an absorption wavelength of a gas of interest, wherein if said gas enters said extended cavity said laser power will be reduced, wherein said cavity is functionalized with a gas-sensitive coating.
2. The method of claim 1, wherein the step of tuning comprises scanning said optical cavity.

3. The method of claim 1, wherein the step of tuning comprises changing the size of said extended coupled cavity.

4. The method of claim 1, wherein said extended cavity comprises a gap, wherein the step of tuning comprises changing the size of said gap.

5. The method of claim 4, wherein said laser includes a gain medium and an anti-reflection coating, wherein said anti-reflection coating is located between said gain medium and said gap to eliminate coupled-cavity effects.

6. The method of claim 1, wherein said extended cavity comprises a gap, wherein the step of tuning comprises changing the size of said gap by altering an electrostatic charge applied across said gap.

7. The method of claim 1, wherein said laser is designed to produce said laser emission light by including an epitaxial materials structure in said laser, wherein said epitaxial materials structure is engineered to align said laser emission light to a specific absorption wavelength of a gas of interest.

8. The method of claim 1, wherein the presence of gas in said extended cavity quenches said laser emission light when the resonance wavelength is tuned to correspond with an appropriate absorption line of said gas.

9. The method of claim 1, wherein said laser comprises epitaxial material.

10. The method of claim 1, wherein said laser comprises dielectric material.

11. The method of 10, wherein said dielectric material comprises a silicon nitride membrane and an evaporated dielectric DBR.

12. The method of claim 11, wherein the step of tuning said optical cavity comprises applying an electrical bias across an aluminum contact on top of said silicon nitride membrane and a p-contact on said laser to create an electrostatic force that displaces said membrane to reduce the cavity size.

13. The method of claim 1, further comprising monitoring said emission light through an optical fiber to a detector.

14. The method of claim 1, further comprising monitoring said emission light directly via an integrated detector.

15. The method of claim 1, wherein said coating comprises a material selected from the group consisting of $WO_3$, $SnO_2$, PdO, ZnO and porous Si.

16. The method of claim 1, wherein the presence of gas in said extended cavity spoils the gain-loss balance necessary for lasing by increasing the absorption losses within said cavity.

* * * * *